United States Patent [19]

Schenkel et al.

[11] Patent Number: 4,710,377

[45] Date of Patent: Dec. 1, 1987

[54] **ANTIGENS AND MONOCLONAL ANTIBODIES REACTIVE AGAINST SPOROZOITES OF *EIMERIA SPP.***

[75] Inventors: Robert H. Schenkel, Yardley, Pa.; Rosie B. Wong, Piscataway; Pallaiah Thammana, Hazlet, both of N.J.

[73] Assignee: American Cyanamid Company, Stamford, Conn.

[21] Appl. No.: 591,288

[22] Filed: Mar. 19, 1984

Related U.S. Application Data

[63] Continuation-in-part of Ser. No. 524,819, Aug. 19, 1983, abandoned.

[51] Int. Cl.[4] .................... G01N 33/53; C12P 21/00; A61K 39/00; A61K 45/02
[52] U.S. Cl. ........................................ 424/88; 424/85; 435/68; 514/2; 514/6; 514/8; 530/350; 530/387; 530/403; 436/548
[58] Field of Search ............... 424/85, 88, 92; 435/68, 435/240, 241, 948; 436/548; 26/112 R

[56] References Cited

U.S. PATENT DOCUMENTS 4,289,690  9/1981  Pestka et al. .................. 260/112 R
4,301,148 11/1981  Shibata et al. ........................ 424/93
4,341,697  7/1982  Snary ............................. 260/112 R

FOREIGN PATENT DOCUMENTS

83/01739  5/1983  PCT Int'l Appl. ................ 435/240

OTHER PUBLICATIONS

Danforth, *Biol. Abst.*, v 75(b), Jun. 1982, No. 42067, "Development of Hybridoma-Produced Antibodies Directed Against *Eimeria tenella* and *Eimeria mitis*.
Nabin, *Chem. Abst.*, v 96, No. 83834f, 1982, "Immunological Control of Parasitic Diseases Through Chemically Pretreated Antigens".
Danforth, *J. Parasitol*, v 68(3), 1982, Jun., pp. 392–397, "Development of Hybridoma-Produced Antibodies Directed Against *Eimeria tenella* and *Eimeria mitis*.
Danforth et al, *Poultry Sci.*, v. 61(7), pp. 1446–1447, Jul. 82, "Crossreactivity of Monoclonal Antibodies Directed Against Various Species of Avian Coccidia".

*Primary Examiner*—Thomas G. Wiseman
*Assistant Examiner*—Robinlyn Teskin
*Attorney, Agent, or Firm*—Estelle J. Tsevdos

[57] ABSTRACT

Monoclonal antibodies against sporozites of the Eimeria spp. are obtained by use of hybridoma technology. Specific sporozoite antigens for use as vaccines in the prevention and treatment of coccidiosis and hybridoma cultures producing monoclonal antibodies are described.

14 Claims, No Drawings

ANTIGENS AND MONOCLONAL ANTIBODIES REACTIVE AGAINST SPOROZOITES OF *EIMERIA SPP.*

This application is a CIP of application Ser. No. 524,819 filed 8/19/83 now abandoned.

The invention herein described relates to monoclonal antibodies which react specifically against sporozoites of the parasite *Eimeria tenella*. Hybridoma cultures producing antibodies against *E. tenella* are described. Such antibodies are obtained by means of hybridoma technology. Sporozoite antigens are identified and characterized. These antigens, along with certain monoclonal antibodies are effective for the prevention and treatment of coccidiosis. The antigens of the invention are useful as vaccines against coccidiosis.

By way of background, coccidiosis is a disease of animals caused by a variety of protozoan parasites. Avian coccidiosis is a devastating disease of poultry caused by a variety of species of the genus Eimeria. This disease has a complicated life cycle consisting of both asexual and sexual stages. Chickens are initially infected with the disease after ingestion of free-living oocysts which are generally associated with fecal material. Oocysts develop into invasive asexual sporozoites in the chicken's digestive tract. The sporozoites infect epithelial cells and develop into multinucleate structures known as schizonts. Each schizont matures and eventually liberates multiple invasive asexual structures known as merozoites. These merozoites leave the infected cell and reinvade other epithelial cells. The multiple invasive asexual stages involving sporozoites and merozoites account for much of the pathology of coccidiosis. The sexual cycle of coccidiosis is initiated when merozoites differentiate into gametocytes. Fertilization occurs and the fertilization products known as oocysts are released in the feces. Thus the parasite's life cycle is completed. In chickens, the life cycle of *Eimeria tenella*, a representative species, is completed in about 7 to 9 days.

Due to the tremendous economic losses inflicted on the poultry industry by Eimeria species, a vaccine against the parasite is highly desirable. However, due to the complexity of the life cycle of the parasite and the variability of the quantity of antigens present in each stage, it has been observed that deactivated or killed parasites have not generated consistent immunity in the past. One solution to this problem is to isolate and characterize particular antigens from the parasite and administer them in a sufficient amount to serve as an immunizing agent. Preferably such antigens will offer protection against infection by all important species. It is known that various species of Eimeria, as well as different stages in the life cycle of the same species, have both common and specific antigens [Cerna, Z., Folia Parasitologica (Prague) 17: 135–140 (1970); Davis et al., Immunol. 34: 879–888 (1978); Rose, M. E., Immunol. 2: 112–122 (1959); Rose et al., Immunol. 5: 79–92 (1962); and Tanielian et al., Acta Parasitol. Yugosl. 7: 79–84 (1976)]. It is also known that development of immunity to Eimeria is species specific and in some species of domestic fowl there is significant strain-specific immunity [Jeffers, T. K.; In Long, P. L. et al. (eds.), Avian Coccidiosis, pp. 57–125, Proc. 13th Poultry Sci. Symp. (1978); Joyner, L. P., Parasitol. 59: 725–732 (1969); Long, P. L., Parasitol. 69: 337–347 (1974); and Long et al., Parasitol. 79: 451–457 (1979)].

Currently immunogens of Eimeria species capable of stimulating protective immunity in avian or mammalian hosts have not yet been isolated or identified. Such Eimeria immunogens will likely provide successful immunization against coccidiosis.

The development of lymphocyte hybridoma technology provides a tool for producing relatively large amounts of specific antibodies against various antigens of Eimeria. By fusing specific antibody-producing cells (spleen cells) with cells of a myeloma tumor, it is possible to produce hybridoma cells that secrete monoclonal antibodies directed specifically against the original sensitizing antigen. [Köhler & Milstein, Nature (London) 256: 495–497 (1975)]. If monoclonal antibodies against the parasite are obtained, it may be possible to provide such anitbodies to infected or susceptible fowl and to thus provide the host organism with a measure of passive immunity. Once such hybridoma cultures producing monoclonal antibodies are obtained, it is possible by various procedures to utilize such antibodies to isolate and identify specific antigens which could in turn be utilized as a vaccine to provide host organisms with a system of active immunity. Various patents concerning hybridoma cultures and monoclonal antibodies are known (i.e., U.S. Pat. Nos. 4,172,124; 4,196,265; 4,271,145; 4,361,549; 4,631,550; 4,364,932; 4,364,933; 4,364,934; 4,364,935; 4,364,936; 4,381,292; and 4,381,295).

In light of the foregoing discussion of the economic effects of coccidiosis in the area of animal husbandry and more specifically in the poultry industry control of the protozoan parasite Eimeria is highly desirable. Accordingly, an object of this invention is to provide new and useful monoclonal antibodies obtained against sporozoites of the genus Eimeria. A further object is to isolate and identify specific antigens of *E. tenella* useful as a vaccine for the control of avian coccidiosis. These objects are manifest in the following description and particularly delineated in the appended claims.

A preparation of *E. tenella* sporozoites is used to immunize mice in order to eventually generate monoclonal antibodies following the method of Köhler and Milstein as described below. The monoclonal antibodies are used to identify antigens of the parasite. The antigens which elicit monoclonal antibodies that react with sporozoites, and show neutralization of parasite growth, are considered protective antigens. The protective antigens that occur in various species of Eimeria are regarded as potential candidates for the development of a vaccine against avian coccidiosis.

Soluble antigens are obtained from sporozoites of *E. tenella*. These soluble antigens are separated electrophoretically by molecular weight and those which specifically react with monoclonal antibodies of the present invention are identified. Using appropriate standards, the reactive antigens are then characterized on the basis of molecular weight.

In order to evaluate the ability of the monoclonal antibodies to effectively neutralize the infective capability of coccidial sporozoites, chickens are exposed to sporozoites of *E. tenalla* previously treated with various monoclonal antibodies of the invention. This in vivo experimental system demonstrates the protective capabilities of selected monoclonal antibodies.

Chickens receiving injections of solubilized sporozoite antigens including those identified by the corresponding monoclonal antibodies are found to be protected against oral challenge. This immunization procedure demonstrates the vaccine potential of sporozoite antigens which can be recognized by monoclonal antibodies.

The following non-limiting Examples further serve to illustrate the invention:

EXAMPLE 1

Construction of Hybridoma Lines

Sporozoites of the organism *Eimeria tenella* are obtained by excysting sporulated oocysts using established procedures [Doran et al., Proc. Helmintol. Soc. Wash. 34: 59–65 (1967)]. A preparation of *E. tenella* sporozoites thus obtained is used to immunize eighteen-week-old female BALB/c mice by intraperitoneal injection. After determining that an immunized mouse is producing anti-sporozoite antibodies using an indirect immunofluorescene assay (IFA) technique known to the art, spleen cells are obtained from the mouse and fused with mouse myeloma cell line P3X63.Ag8.653. The fusion process is carried out in the presence of 30 to 35% polyethylene glycol (950–1050). The method of generating hybridomas has been previously described (c.f., Kennett et al., Monoclonal Antibodies—Plenum Press: 365–371, 1980). Hybridoma fusion products are cultured in HAT medium [Littlefield, J. W., Science, 145: 709–710 (1964)] containing Iscove's modified Dulbecco's medium (IMDM) with 20% fetal calf serum supplement. Culture media are monitored for anti-sporozoite antibody production by indirect immunofluorescence assay (IFA) using glutaraldehyde fixed sporozoites of *E. tenella* as the antigen source. Of all the cultures tested, 33 wells are found positive by IFA.

In order to ensure monoclonicity of the hybridoma cultures, a limiting dilution procedure was employed. Following exposure of *E. tenella* sporozoites to various monoclonal antibodies of the invention, three major IFA reactivity patterns on treated sporozoites are observed: (1) reaction on the entire surface of sporozoites; (2) surface reaction as patches on the sporozoites; (3) internal reaction around the nuclear membranes of sporozoites. These reaction patterns are confirmed by ferritin labelling and transmission election microscopy (Speer et al., J. of Protozoology in press). As assessed by IFA, hybridoma cultures of the invention generate identical antibodies after cloning. Clones are grown either in vitro or in BALB/c mice as peritoneal tumors and the ascites fluid contains antibodies in a concentration of up to approximately 10 mg/ml.

EXAMPLE 2

Preparation of Antigens Associated with *E. tenella* sporozoites

Freshly excysted sporozoites of *E. tenella* are used for the antigen preparation. The outer membrane components of the sporozoites are extracted using detergents (i.e., 0.5% Nonidet P40, 0.5 to 2% CHAPS, or 0.5% to 1% Triton X-100) in 5 mM sodium phosphate buffer having a pH of 7.8. The buffer contains the following protease inhibitors: aprotinin (2 trypsin units/ml); antipain (25 µg/ml); leupeptin (25 µg/ml), phenyl methyl sulfonyl fluoride (4 mM) [Yoshida et al., J. Exp. Med., 154: 1225–1236 (1981)]. The detergent solubilized material is centrifuged at 100,000×g for 10 minutes to remove particulate matter. The clear supernatant contains soluble antigens associated with *E. tenella* sporozoites.

EXAMPLE 3

Antigen Characterization

Soluble antigens of *E. tenella* sporozoites are separated by molecular weight using SDS polyacrylamide gel electrophoresis (PAGE) [Laemmli, U.K., Nature 227: 680–685 (1970)]. The SDS PAGE separated proteins are transferred electrophoretically onto nitrocellulose membranes using the Western blotting technique [Towbin et al., Proc. Natl. Acad. Sci. (USA) 76: 4350–4354 (1979)]. The nitrocellulose filter is then reacted with either diluted ascites fluid or spent hybridoma culture fluid containing antibodies. Bound monoclonal antibodies are then detected by using a radioimmuno detection method involving $^{125}I$ labelled anti-mouse IgG antibody (New England Nuclear). The unbound second antibody is removed by washing, and the nitrocellulose filters are then exposed with Kodak X-ray film XAR-5.

Alternatively, specific antigen-monoclonal antibody complexes are identified by an ELISA technique using horseradish peroxidase coupled rabbit IgG antibody (Cappel Lab) against mouse immunoglobulin [Burnette et al., Anal. Biochem. 112: 195–203 (1981)]. The Bio-Rad Immuno Blot Assay Kit is employed.

The apparent molecular weights of the reactive sporozoite antigens are determined by comparing the electrophoretic Rf values of the antigens with Rf values of known molecular weight compounds run as standards along with the antigens in the same system. The experimental molecular weight data of various antigens are presented in Table I.

TABLE I

| MOLECULAR WEIGHT DETERMINATION OF VARIOUS *E. TENELLA* SPOROZOITE ANTIGENS | | |
|---|---|---|
| Hybridoma Culture | Monoclonal Antibody | Approximate Molecular Weight of Antigen |
| s5E5 | s1 | 110 ± 16, 130 ± 20 kd |
| s4E2 | s2 | 110 ± 16, 130 ± 20 kd |
| s1C4 | s3 | 66 ± 9 kd, 55 ± 8 kd, 20 – 30 kd, 18 ± 3 kd, 15 ± 2 kd |
| s2G8 | s4 | 55 ± 8 kd |
| s5B9 | s5 | 55 ± 8 kd |
| s1A | s6 | 54 ± 8 kd |
| s3C11 | s7 | 50 ± 7 kd |
| s3D3 | s8 | 29 ± 4 kd |
| s1E4 | s9 | 58 ± 9 kd, 130 ± 20 kd |

EXAMPLE 4

Neutralization of Sporozoites of *E. tenella* With Monoclonal Antibodies Using In Vivo Chicken Assay An in vivo system is employed to evaluate the capability of monoclonal antibodies produced from hybridoma lines of the invention to neutralize sporozoites of *E. tenella*. The caeca of the fowl are the sites of infection by *E. tenella* and are accessable by surgery [Burns et al., Exp. Parasitol 8: 515–526 (1959); Lawn et al., J. Parasitol. 68: 1117–1123 (1982)]. The caeca of chickens are surgically exposed and infused with preparations of *E. tenella* sporozoites which have been previously treated with monoclonal antibodies of the invention.

Freshly excysted sporozoites are incubated under sterile conditions with heat inactivated ascites fluid ontaining monoclonal antibodies derived from hybridoma lines of the invention. The incubation period is for 30 to 60 minutes at 25° to 37° C. An incubation period of 37° C. for 60 minutes is preferred. Treated sporozoites are then introduced into the caeca of three-week-old chickens by surgical procedures. At the end of a five-day incubation period, the caeca of the infected chickens are observed for lesions. The five-day incubation period represents the most destructive stage of coccidiosis. Results of this experiment are presented in Table II. It is noted that monoclonal antibodies s3 and s8 both provided 60% total protection against infection by sporozoites of E. tenella.

TABLE II

IN VIVO EVALUATION OF VARIOUS MONOCLONAL ANTIBODIES FOR THE CONTROL OF SPOROZOITES OF E. TENELLA

| Treatment Hybridoma Line (source of monoclonal antibody) | Monoclonal Antibody No. | Number of Sprozoites | % Protection | | |
|---|---|---|---|---|---|
| | | | None | Partial | Complete |
| — | — | 2000 | 70 | 21 | 9 |
| s3D3 | s8 | 2000 | 30 | 10 | 60 |
| s2G8 | s4 | 2000 | 100 | 0 | 0 |
| s1C4 | s3 | 2000 | 20 | 20 | 60 |
| s1E4 | s9 | 2000 | 60 | 0 | 40 |
| s3D3 & s2G8 | s8 + s4 | 2000 | 25 | 19 | 56 |
| s3D3 & s1C4 | s8 + s3 | 2000 | 75 | 0 | 25 |
| — | — | 3000 | 89 | 11 | 0 |
| s3D3 | s8 | 3000 | 60 | 40 | 0 |
| s2G8 | s4 | 3000 | 67 | 16 | 16 |
| s1C4 | s3 | 3000 | 50 | 0 | 50 |
| s1E4 | s9 | 3000 | 100 | 0 | 0 |
| s3D3 & s2G8 | s8 + s4 | 4000 | 50 | 50 | 0 |
| s3D3 & s1C4 | s8 + s3 | 3000 | 50 | 0 | 50 |
| s3D3 & s1A | s8 + s6 | 3000 | 80 | 0 | 20 |

EXAMPLE 5

Immunization with E. tenella sporozoite antigens

Chickens at one week of age were immunized intraperitoneally with solubilized E. tenella sporoziote antigens. Initial injections employed proteinaceous material derived from $1.5 \times 10^7$ sporoziotes in Freund's complete adjuvant. Two boosters followed at ten-day intervals each employing one-half the initial immunizing dose of material in Freund's incomplete adjuvant. Ten days after the last booster, the chickens were challenged with 50,000 oocysts orally. Five days post-challenge, caecal lesions were observed. Results on this experiment are presented in Table III. It is noted that soluble antigens render significant protection against oral oocyst challenge whereas normal chickens are not protected.

TABLE III

| | Percent protection (% of birds tested) | | |
|---|---|---|---|
| Treatment | None | Partial | Complete |
| Control | 100 | 0 | 0 |
| Immunized | 0 | 33 | 66 |

The new monoclonal antibodies, No. s1C4, No. s3D3, No. s1E4, No. s5B9, No. s5E5, No. s1A and No. s2G8, isolated as described hereinabove, have been deposited with the American Type Culture Collection (ATCC) located in Rockville, Md. and have been added to its permanent collection. No. s1C4 has been assigned the number HB8333; No. s3D3 has the number HB8331; No. s1E4 has been designated the number HB8332, No. s5B9 has been designated number HB8402, No. s5E5 has been designated number HB8403, No. s1A has been designated number HB8404 and No. s2G8 has been designated number HB8405. Access to the antibodies are available during the pendency of the present application to one determined by the Commissioner of Patents and Trademarks to be entitled thereto under 37 C.F.R. 1.14 and 35 U.S.C. 122, and all restrictions on the availability to the public of HB8331, HB8332, HB8333, HB8402, HB8403, HB8404 and HB8405 will be irrevocably removed upon the granting of a patent on the present application.

What is claimed is:

1. Monoclonal antibodies produced by hybridomas formed by fusion from mouse myeloma line P3X63.Ag8.653 cells and spleen cells from BALB/c mouse previously immunized with Eimeria tenella sporozoites, which antibody:
   (a) reacts specifically with antigens of Eimeria spp. sporozoites;
   (b) reacts specifically with antigens of Eimeria tenella having a molecular weight of approximately 13 to 150 Kd; and
   (c) is produced by the hybridomas designated clone number s1C4 and deposited as ATCC number HB8333; hybridoma designated clone number s3D3 and deposited as ATCC number HB8331; and hybridoma designated clone number s1E5 and deposited as ATCC number HB8332.

2. A method of preparing monoclonal antibodies which react with antigens of Eimeria spp. sporozoites which comprises culturing clone number s5E5 (ATCC No. HB8403), s1C4 (ATCC No. HB8333), s2G8 (ATCC No. HB8405), s5B9 (ATCC No. HB8403), s1A (ATCC No. HB8404), s3D3 (ATCC No. HB8331), or s1E4 (ATCC No. HB8332), in a suitable medium and recovering the antibody from the supernatant of an above said hybridoma culture.

3. A monoclonal antibody prepared by the method of claim 2.

4. A method of preparing monoclonal antibodies which react with antigens of Eimeria spp. sporozoites which comprises injecting into a mouse a hybridoma culture designated clone No. s5E5 (ATCC No. HB8403), s1C4 (ATCC No. HB8333), s2G8 (ATCC No. HB8405), s5B9 (ATCC No. HB8402), s1A (ATCC No. HB8404), s3D3 (ATCC No. HB8331), or s1E4 (ATCC No. HB8332) and recovering said antibody from the ascites or serum of said mouse.

5. A monoclonal antibody prepared by the method of claim 4.

6. A proteinaceous vaccine which comprises: anticoccicidally-effective amounts of Eimeria tenella sporozoite antigen consisting essentially of antigens of $110 \pm 16$ Kd and $130 \pm 20$ Kd molecular weight which react with antisporozoite monoclonal antibody produced by s5E5 (ATCC No. HB8493); and wherein said antigen is soluble in detergent containing buffer.

7. A proteinaceous vaccine which comprises: anticoccidially-effective amounts of *Eimeria tenella* sporozite antigen consisting essentially of antigens of 66±9 Kd, 55±8 Kd, 20–30 Kd, 18±3 Kd, 15±2 Kd molecular weight which react with antisporozoite monoclonal antibody produced by s1C4 (ATCC No. HB8333); and wherein said antigen is soluble in detergent containing buffer.

8. A proteinaceous vaccine which comprises: anticoccidially-effective amounts of *Eimeria tenella* sporozoite antigen consisting essentially of antigens of 55±8 Kd molecular weight which react with antisporozoite monoclonal antibody produced by s2G8 (ATCC No. HB8405); and wherein said antigen is soluble in detergent containing buffer.

9. A proteinaceous vaccine which comprises: anticoccidially-effective amounts of *Eimeria tenella* sporozoite antigen consisting essentially of 55±8 Kd molecular weight which react with antisporozoite monoclonal antibody produced by s5B9 (ATCC No. HB8402); and wherein said antigen is soluble in detergent containing buffer.

10. A proteinaceous vaccine which comprises: anticoccidially-effective amounts of *Eimeria tenella* sporozoite antigen consisting essentially of antigens of 54±8 Kd molecular weight which react with antisporozoite monoclonal antibody produced by s1A (ATCC No. HB8404); and wherein said antigen is soluble in detergent containing buffer.

11. A proteinaceous vaccine which comprises: anticoccidially-effective amounts of *Eimeria tenella* sporozoite antigen consisting essentially of antigens of 29±4 Kd molecular weight which react with antisporpzoite monoclonal antibody produced by s3D3 (ATCC No. HB8331); and wherein said antigen is soluble in detergent containing buffer.

12. A proteinaceous vaccine which comprises: anticoccidially-effective amounts of *Eimeria tenella* sporozoite antigen consisting essentially of antigens of 58±9 Kd and 130±20 Kd molecular weight which react with antisporozoite monoclonal antibody produced by s1E4 (ATCC No. HB8332); and wherein said antigen is soluble in detergent containing buffer.

13. A proteinaceous vaccine according to claims 6, 7, 8, 9, 10, 11 or 12 additionally containing a stabilizer and/or pharmaceutically acceptable adjuvant thereof.

14. A method of combating *Eimeria tenella* infection which comprises: administering intraperitoneally, orally or intramuscularly into domestic species, one or a combination of antigens reactive with anti-sporozoite monoclonal antibodies secreted by hybridoma clone s5E5 (ATCC No. HB8403), s1C4 (ATCC No. HB8333), s2G8 (ATCC No. HB8405), s5B9 (ATCC No. HB8402), s1A (ATCC No. HB8404), s3D3 (ATCC No. HB8331), s1E4 (ATCC No. HB8332) or mixtures thereof; wherein about 3 ng to 30 ug of said combination of antigens is administered to said domestic species.

* * * * *